United States Patent
Tomatsu et al.

(10) Patent No.: US 9,161,690 B2
(45) Date of Patent: Oct. 20, 2015

(54) OPHTHALMOLOGIC APPARATUS AND CONTROL METHOD OF THE SAME

(75) Inventors: Nobuhiro Tomatsu, Yokohama (JP); Tomoyuki Makihira, Tokyo (JP); Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 36 days.

(21) Appl. No.: 13/409,607

(22) Filed: Mar. 1, 2012

(65) Prior Publication Data

US 2012/0229764 A1 Sep. 13, 2012

(30) Foreign Application Priority Data

Mar. 10, 2011 (JP) ................................. 2011-052296

(51) Int. Cl.
*A61B 3/14* (2006.01)
*A61B 3/00* (2006.01)
*A61B 3/10* (2006.01)
*A61B 3/113* (2006.01)

(52) U.S. Cl.
CPC ................ *A61B 3/113* (2013.01); *A61B 3/0058* (2013.01)

(58) Field of Classification Search
CPC .......... A61B 3/103; A61B 3/14; A61B 3/113; A61B 3/1225; A61B 3/1015; A61B 3/12
USPC ......... 351/206, 200, 205, 210, 211, 221, 246, 351/209
See application file for complete search history.

(56) References Cited

U.S. PATENT DOCUMENTS

| 5,943,116 A * | 8/1999 | Zeimer ........................ 351/221 |
| 6,588,901 B1 * | 7/2003 | Grinvald et al. .............. 351/206 |
| 7,258,443 B2 | 8/2007 | Masaki |
| 7,789,511 B2 | 9/2010 | Aoki et al. |
| 2005/0119642 A1 | 6/2005 | Grecu et al. |
| 2005/0275804 A1 * | 12/2005 | Masaki ........................ 351/208 |
| 2006/0119794 A1 | 6/2006 | Hillis et al. |
| 2006/0228011 A1 | 10/2006 | Everett et al. |
| 2006/0239670 A1 | 10/2006 | Cleveland |
| 2007/0222945 A1 * | 9/2007 | Tsukada et al. ............... 351/205 |
| 2008/0007691 A1 * | 1/2008 | Mihashi et al. ............... 351/206 |
| 2008/0259275 A1 | 10/2008 | Aoki et al. |
| 2010/0110275 A1 | 5/2010 | Mathieu |

(Continued)

FOREIGN PATENT DOCUMENTS

| CN | 1254261 A | 5/2000 |
| CN | 1305354 A | 7/2001 |

(Continued)

OTHER PUBLICATIONS

Jun. 5, 2012 European Search Report in European Patent Appln. No. 12158660.6.

(Continued)

*Primary Examiner* — Dawayne A Pinkney
(74) *Attorney, Agent, or Firm* — Fitzpatrick, Cella, Harper & Scinto

(57) ABSTRACT

There is provided an ophthalmologic apparatus having a tracking function that can select a fundus image that is less affected by eye motion to reduce burdens on an operator/a patient in fundus imaging, wherein the ophthalmologic apparatus picks up a first fundus image (202), extracts a characteristic point as a template from the first fundus image (203), executes pattern matching on a second fundus image (205) to determine presence/absence of eye motion, and decides a tracking template image (207).

16 Claims, 11 Drawing Sheets

(56) References Cited

U.S. PATENT DOCUMENTS

| | | |
|---|---|---|
| 2010/0226553 A1 | 9/2010 | Suehira |
| 2010/0226554 A1 | 9/2010 | Suehira |
| 2010/0290006 A1 | 11/2010 | Flanagan et al. |
| 2010/0321700 A1 | 12/2010 | Hirose et al. |
| 2011/0058175 A1 | 3/2011 | Suehira |
| 2011/0096333 A1 | 4/2011 | Suehira et al. |
| 2011/0098560 A1 | 4/2011 | Suehira et al. |
| 2011/0116045 A1* | 5/2011 | Utagawa ..................... 351/210 |
| 2011/0211057 A1 | 9/2011 | Iwase et al. |
| 2011/0299035 A1 | 12/2011 | Suehira |
| 2012/0002166 A1 | 1/2012 | Tomatsu et al. |
| 2012/0044499 A1 | 2/2012 | Shimoyama et al. |
| 2012/0133950 A1 | 5/2012 | Suehira et al. |
| 2013/0010259 A1* | 1/2013 | Carnevale ..................... 351/206 |

FOREIGN PATENT DOCUMENTS

| | | |
|---|---|---|
| CN | 1714740 A | 1/2006 |
| CN | 101133943 A | 3/2008 |
| CN | 101681021 A | 3/2010 |
| CN | 101742958 A | 6/2010 |
| JP | 10-234674 A | 9/1998 |
| JP | 2010-110556 A | 5/2010 |
| JP | 4466968 B2 | 5/2010 |
| KR | 10-0684302 B1 | 2/2007 |
| WO | 03/053228 A2 | 7/2003 |
| WO | 2010/052929 A1 | 5/2010 |

OTHER PUBLICATIONS

Hammer, Daniel X., et al., "Image stabilization for scanning laser ophthalmoscopy", Optics Express, vol. 10, No. 26, Dec. 30, 2002, pp. 1542-1549.

Mar. 5, 2014 Chinese Office Action in Chinese Patent Appln. No. 201210063575.9.

Sep. 29, 2014 Chinese Official Action in Chinese Patent Appln. No. 201210063575.9.

* cited by examiner

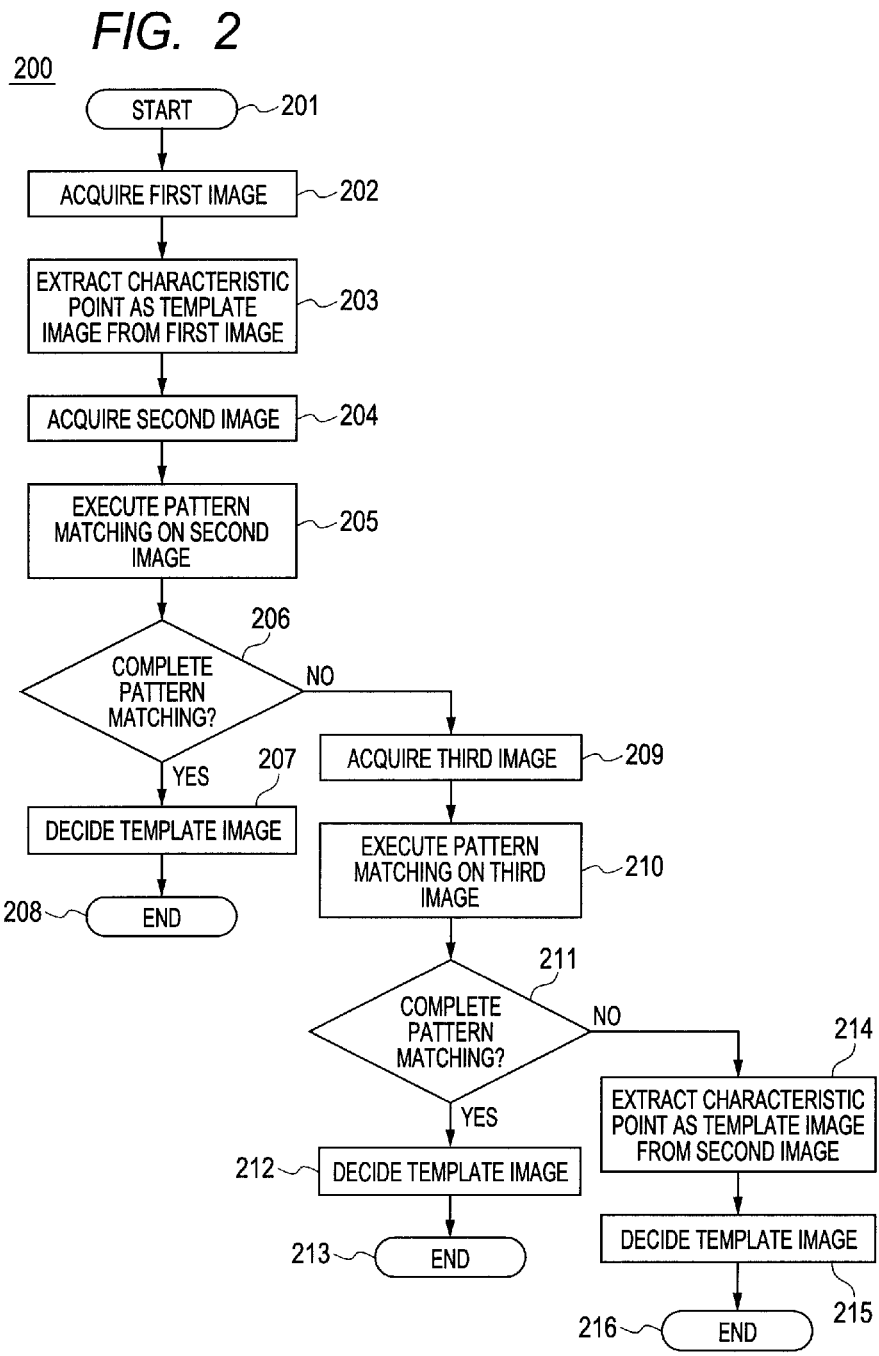

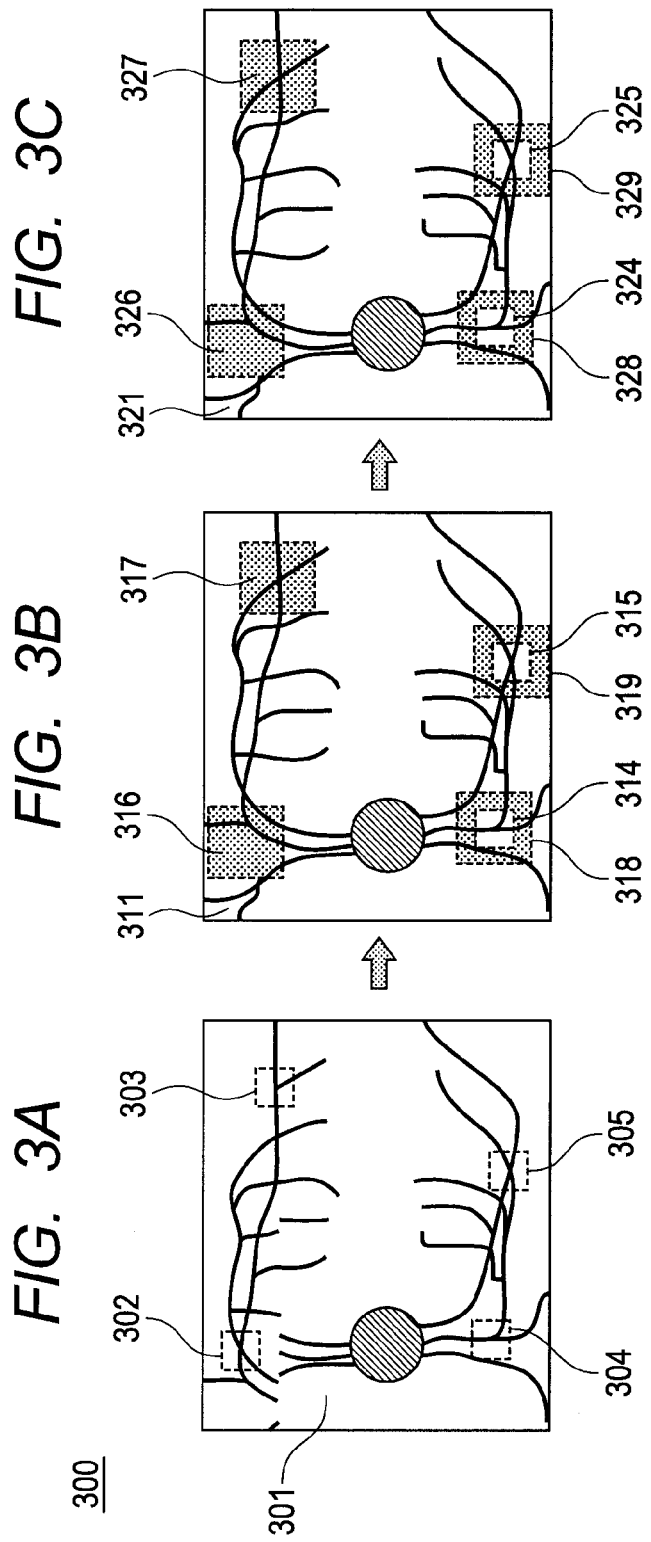

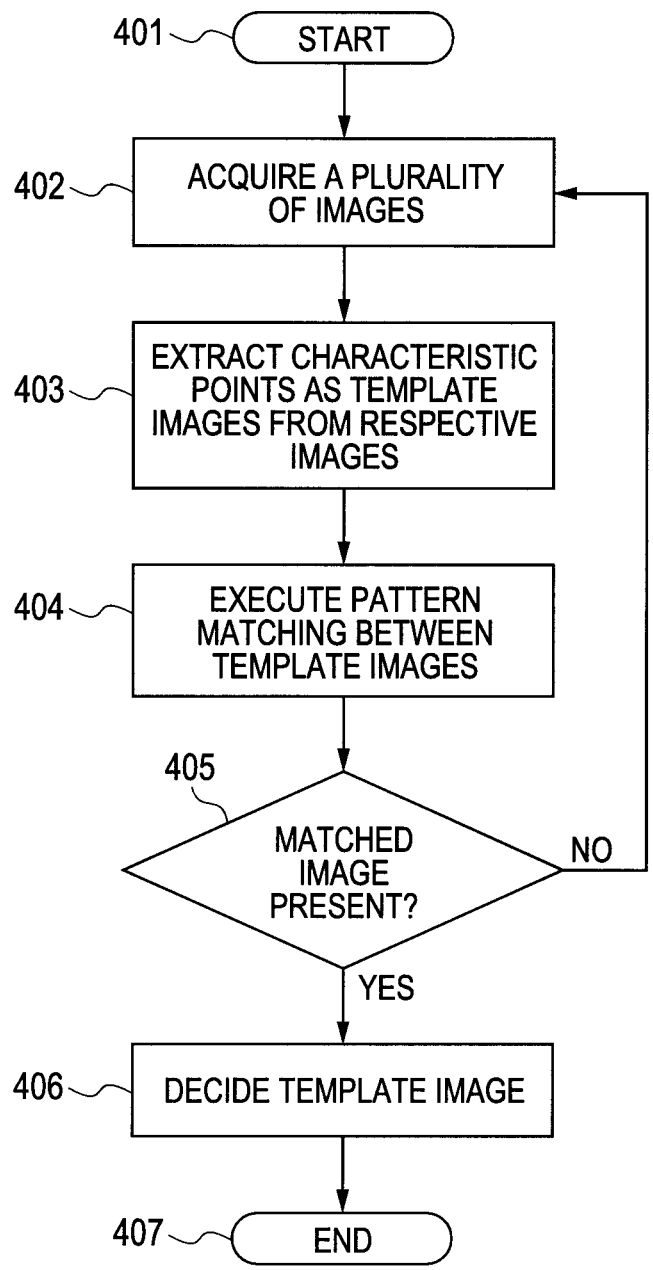

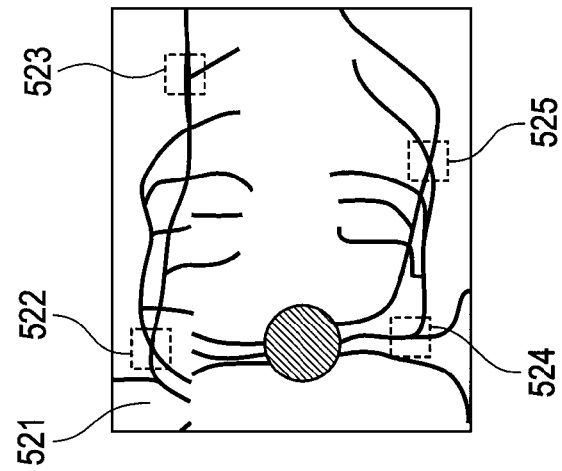
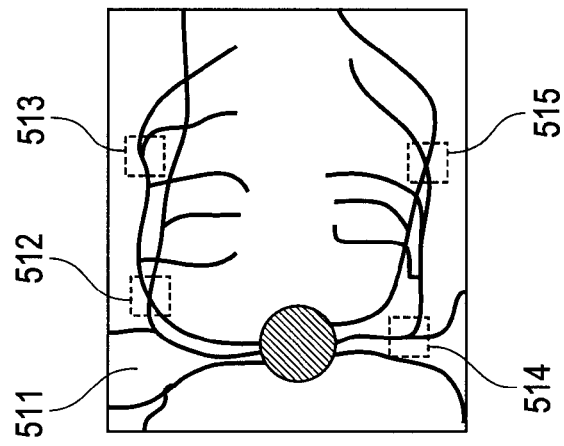
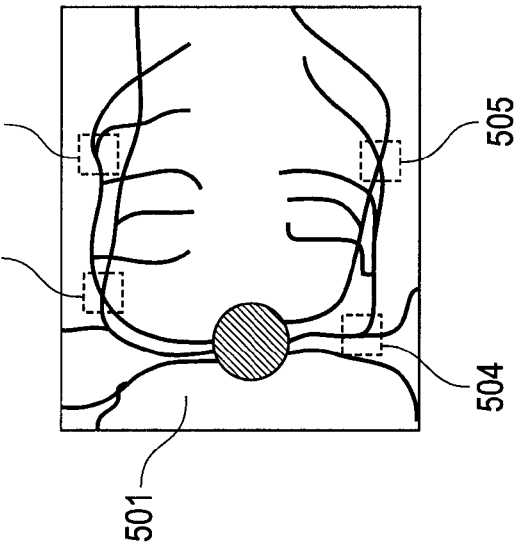

FIG. 6A

| FIRST AREA | | | |
|---|---|---|---|
| | 502 | 512 | 522 |
| 502 | | ○ | ○ |
| 512 | ○ | | ○ |
| 522 | ○ | ○ | |

FIG. 6B

| SECOND AREA | | | |
|---|---|---|---|
| | 503 | 513 | 523 |
| 503 | | ○ | × |
| 513 | ○ | | × |
| 523 | × | × | |

FIG. 6C

| THIRD AREA | | | |
|---|---|---|---|
| | 504 | 514 | 524 |
| 504 | | ○ | ○ |
| 514 | ○ | | ○ |
| 524 | ○ | ○ | |

FIG. 6D

| FOURTH AREA | | | |
|---|---|---|---|
| | 505 | 515 | 525 |
| 505 | | ○ | ○ |
| 515 | ○ | | ○ |
| 525 | ○ | ○ | |

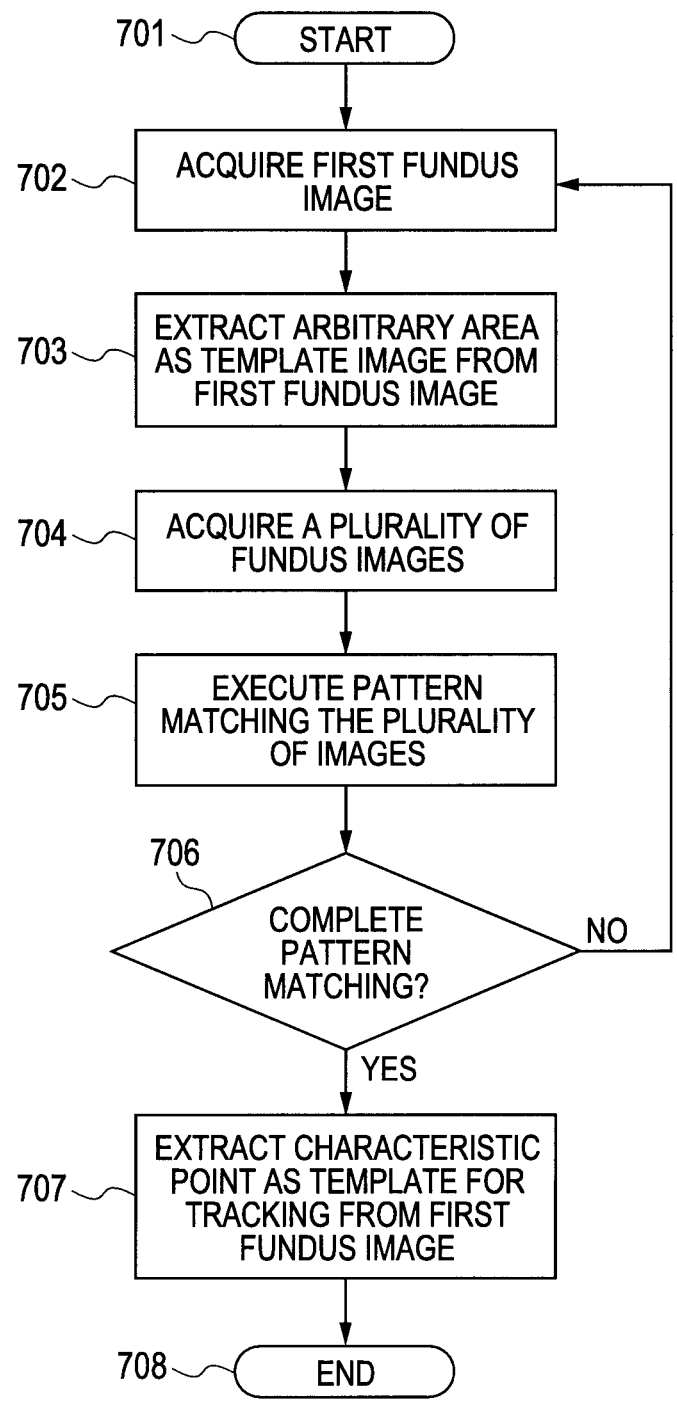

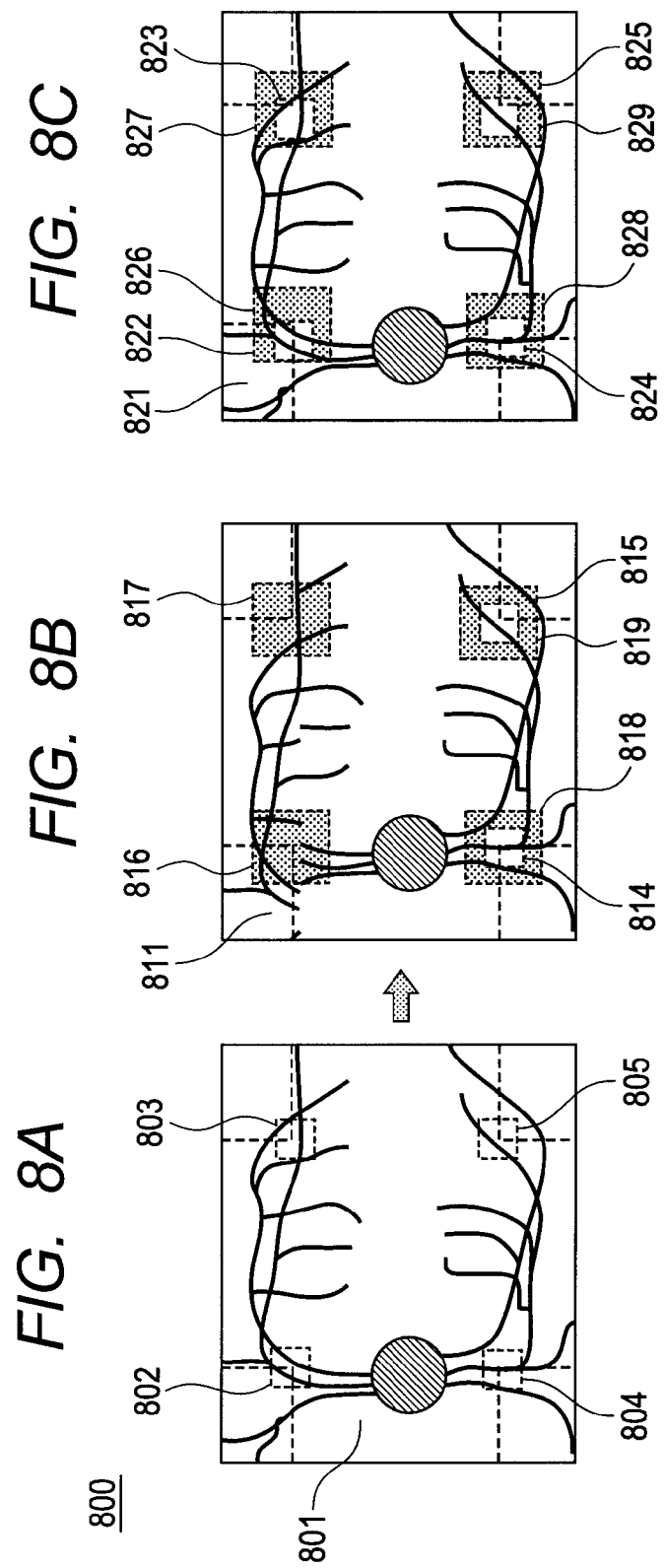

| TEMPLATE | X COORDINATE | Y COORDINATE |
|---|---|---|
| 802 | −750 | 750 |
| 803 | 750 | 750 |
| 804 | −750 | −750 |
| 805 | 750 | −750 |

| TEMPLATE | SEARCHING POINT | |
|---|---|---|
| 302 | 316 | 326 |
| 303 | 317 | 327 |
| 304 | 318 | 328 |
| 305 | 319 | 329 |

FIRST AREA

|   | 816 | 826 |
|---|---|---|
| 802 | × | ○ |

FIG. 11B

SECOND AREA

|   | 817 | 827 |
|---|---|---|
| 803 | × | ○ |

FIG. 11C

THIRD AREA

|   | 818 | 828 |
|---|---|---|
| 804 | ○ | ○ |

FIG. 11D

FOURTH AREA

|   | 819 | 829 |
|---|---|---|
| 805 | ○ | ○ |

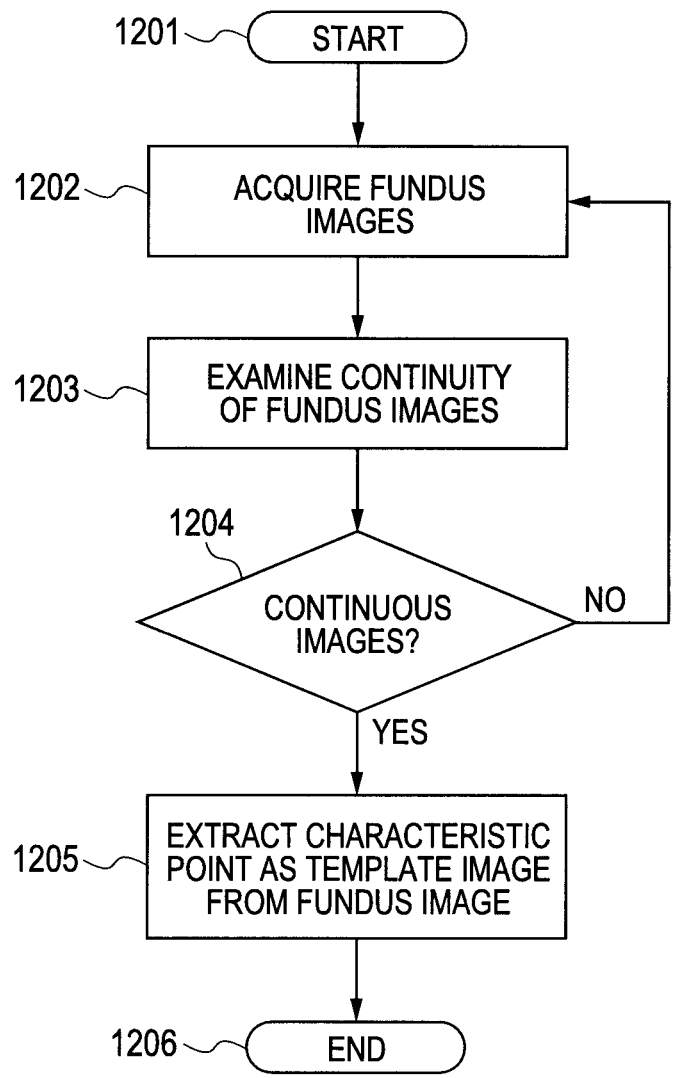

OPHTHALMOLOGIC APPARATUS AND CONTROL METHOD OF THE SAME

BACKGROUND OF THE INVENTION

1. Field of the Invention

The present invention relates to an ophthalmologic apparatus and a control method thereof, and more particularly to an ophthalmologic apparatus that evaluates a fundus image used for extracting a template image in the case where pattern matching of a fundus image is executed in detection of biological motion, and a control method thereof.

2. Description of the Related Art

In recent years, ophthalmologic images typified by fundus images have been used in medical practice as medical images for early detection of diseases. However, in medical practice using ophthalmologic images, the influence of eye movement during photographing has been recognized as a serious problem for long years. Specifically, eye movement may reduce clarity of ophthalmologic images to prevent an increase in accuracy of diagnosis or treatment. Human eyes are repeating involuntary slight vibration even during fixation on one point. This is referred to as involuntary eye movement. Since a patient cannot consciously stop involuntary eye movement, the influence of involuntary eye movement needs to be eliminated on the side of a medical practice tool or an operator in diagnosis or treatment of eyes.

For medical practice with high quality, it is important to eliminate involuntary eye movement without depending on operator's skills. For this purpose, a medical practice tool needs to have measures against eye movement. For example, as disclosed in a document "Daniel X. Hammer, R. Daniel Ferguson, John C. Magill, and Michael A. White, 'Image stabilization for scanning laser ophthalmoscopy', OPTICS EXPRESS 10(26), 1542-1549 (2002)", a tracking technique of applying a light to optic disk in a circular motion, and detecting and correcting eye movement by variation of reflection.

However, the technique disclosed in the document troublesomely requires addition of hardware for detecting eye movement besides an ophthalmoscope. Thus, a tracking method that can be realized without additional hardware for detecting eye movement is suggested as disclosed in Japanese Patent Application Laid-Open No. H10-234674. This is a method of detecting movement of fundus in a lateral direction (a direction perpendicular to an eye depth direction) using a fundus observation apparatus, which is generally included in an ophthalmoscope for alignment, and executing tracking.

Also, as disclosed in Japanese Patent No. 04466968, a method is also proposed of scanning fundus to pick up tomographic images of fundus in a vertical direction (an eye depth direction) in positions shifted with time, and detecting eye movement using three-dimensional images synthesized from the tomographic images in a tomographic imaging apparatus.

Generally, in executing tracking, a small area having a certain characteristic is extracted from an entire fundus image, and movement of the small area between a plurality of continuous fundus images can be detected to detect movement of the entire fundus. With this method, a smaller amount of calculation is required than that in detecting movement of the entire fundus, thereby efficiently detecting movement of the fundus. An image of a small area having a certain characteristic used at this time is referred to as a template image, and a technique of pattern matching is used to detect movement of the template image. The pattern matching is a technique of searching an area most similar to the template image from the entire image to be referred to.

In detecting movement of fundus in pattern matching using a template image, a selected template image does not match an area to be detected or matches an area that is not to be detected in some cases, thereby causing false detection. Thus, a template image has to be properly selected. Also, in order to properly select a template image, it is important that a fundus image from which a template image is extracted is a proper image including no eye motion.

As described above, for the tracking technique by pattern matching, selection of a fundus image for extraction of a template image is very important. However, in the conventional method, whether a fundus image is a proper image is not determined in extraction of a template image. Thus, if pattern matching is not completed, a template image needs to be again extracted during imaging, which increases time and work for extracting a template image, and inevitably places burdens on an operator and a patient.

According to Japanese Patent Application Laid-Open No. H10-234674 above, a method is disclosed of selecting a plurality of small areas having a characteristic from a fundus image and executing matching on fundus images picked up thereafter to detect changes of the fundus images with time. However, determining whether a fundus image from which a small area is selected includes eye motion is not disclosed. Thus, it cannot be determined whether the small area is proper, and a small area needs to be again selected when matching is not completed, which increases burdens on an operator and a patient.

According to Japanese Patent No. 04466968, a technique is disclosed of synthesizing a plurality of tomographic images of fundus picked up in positions laterally shifted with time to once configure a three-dimensional image, and acquiring a lateral two-dimensional image of the fundus from the three-dimensional image to detect movement of the fundus. However, since a step is necessary of acquiring and synthesizing a plurality of tomographic images and further converting the images into a lateral image of the fundus, the movement cannot be detected at high speed during imaging. Also, Japanese Patent No. 04466968 does not disclose a technique of extracting a template image to execute tracking.

SUMMARY OF THE INVENTION

In view of the above problems, the present invention has an object to select a fundus image that is less affected by eye motion in extraction of a template image.

The present invention has another object to shorten an imaging time by selecting a fundus image that is less affected by eye motion.

To achieve the above objects, the present invention provides an ophthalmologic apparatus configured as described below and a control method thereof.

The present invention provides an ophthalmologic apparatus that detects movement of an eye to be inspected using a template image extracted from a fundus image of the eye to be inspected, including: an acquiring unit that scans the eye to be inspected with a measuring light to acquire a fundus image of the eye to be inspected; and a determination unit that determines whether the acquired fundus image is a fundus image affected by movement of the eye to be inspected, wherein the template image is an image extracted from a fundus image determined to be not affected by the determination unit.

The present invention also provides a control method of an ophthalmologic apparatus of detecting movement of an eye to be inspected using a template image extracted from a fundus image of the eye to be inspected, including: acquiring a fundus image from the eye to be inspected; and determining whether the fundus image is affected by movement of the eye to be inspected, wherein the template image is an image extracted from a fundus image determined to be not affected in the determining.

According to the present invention, a fundus image can be selected that is less affected by eye motion in extraction of a template image.

Further features of the present invention will become apparent from the following description of exemplary embodiments with reference to the attached drawings.

BRIEF DESCRIPTION OF THE DRAWINGS

FIG. 2 illustrates a flow for deciding a tracking template in Embodiment 1 of the present invention.

FIGS. 3A, 3B and 3C illustrate evaluation of a fundus image in Embodiment 1 of the present invention.

FIG. 4 illustrates a flow for deciding a tracking template in Embodiment 2 of the present invention.

FIGS. 5A, 5B and 5C illustrate evaluation of a fundus image in Embodiment 2 of the present invention.

FIG. 6A, 6B, 6C and 6D illustrate evaluation of the fundus image in Embodiment 2 of the present invention.

FIG. 7 illustrates a flow for deciding a tracking template in Embodiment 3 of the present invention.

FIGS. 8A, 8B and 8C illustrate evaluation of a fundus image in Embodiment 3 of the present invention.

FIG. 9 illustrates a template image for evaluating an image in Embodiment 3 of the present invention.

FIG. 10 illustrates a searching point in Embodiment 1 of the present invention.

FIGS. 11A, 11B, 11C and 11D illustrate evaluation of the fundus image in Embodiment 3 of the present invention.

FIG. 12 illustrates a flow for deciding a tracking template in Embodiment 4 of the present invention.

DESCRIPTION OF THE EMBODIMENTS (Embodiment 1)

An embodiment of the present invention will be described in detail with reference to the drawings.

In this embodiment, a scanning laser ophthalmoscope (SLO) to which the present invention is applied will be described. In particular, an apparatus will be herein described that extracts a template image from a picked-up first fundus image, and executes pattern matching on a further picked-up second fundus image to evaluate a fundus image, and decides a template image for movement detection of an eye to be inspected for tracking. However, the present invention is not limited to this, but includes a method of evaluating an image using one or more fundus images with respect to the extracted template image (also referred to as a characteristic image).

(Fundus Image Photographing Apparatus: SLO)

Figure 1:
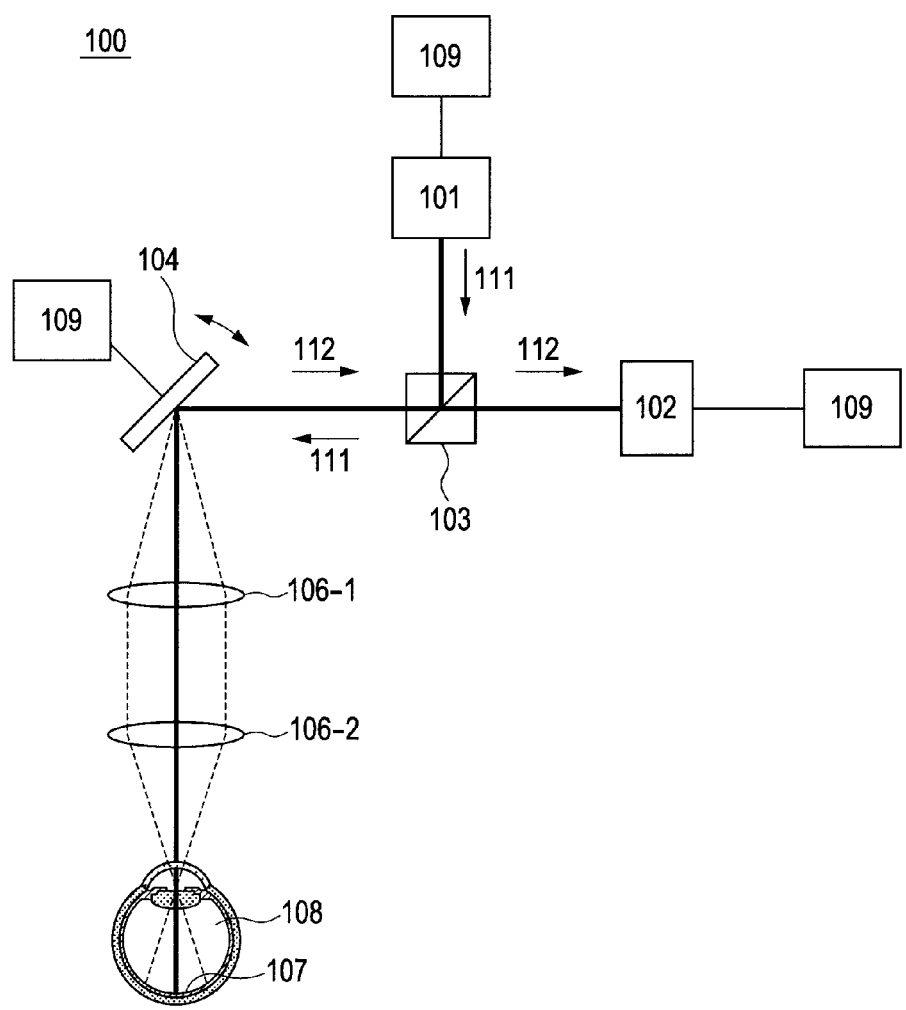
FIG. 1 illustrates a configuration of an ophthalmologic imaging apparatus according to Embodiment 1 of the present invention.

First, with reference to FIG. 1, an entire schematic configuration of an optical system of a scanning laser ophthalmoscope (SLO: Scanning Laser Ophthalmoscope) in this embodiment will be described.

FIG. 1 shows a plurality of memory-control-signal processing units 109 for convenience of drawing, but these memory-control-signal processing units 109 are actually the same component.

An illumination light 111 as a measuring light emitted from a light source 101 is deflected by a half mirror 103, and scanned by an XY scanner 104. The XY scanner 104 corresponds to a scanning unit in the present invention. Between the XY scanner 104 and an eye to be inspected 108, lenses 106-1 and 106-2 for applying the illumination light 111 to fundus 107 are placed. For simplicity, the XY scanner 104 is shown as one mirror, but actually, two mirrors: an X scanning mirror and a Y scanning mirror are placed close to each other. Thus, the XY scanner 104 can execute raster scanning of the fundus 107 perpendicularly to an optical axis.

The illumination light 111 entering the eye to be inspected 108 is reflected or scattered by the fundus 107, and returned as a return light 112. The return light 112 again enters the half mirror 103, and a light transmitted herein enters a sensor 102. The sensor 102 converts light intensity of the return light 112 at each measuring area on the fundus 107 into a voltage, and transmits a signal indicating the voltage to the memory-control-signal processing unit 109. The memory-control-signal processing unit 109 functions as an acquiring unit that generates a two-dimensional fundus image using the transmitted signal, scans the eye to be inspected with the measuring light, and acquires a fundus image of the eye to be inspected. Further, the memory-control-signal processing unit 109 extracts a characteristic area including a crossing/branching region of blood vessels from the fundus image as a template image. Pattern matching on a newly generated fundus image is executed with the extracted template image to detect movement of the eye to be inspected (calculation of an amount of movement). Further, the memory-control-signal processing unit 109 controls a scanning angle of the XY scanner 104 depending on the calculated amount of movement to execute tracking.

The memory-control-signal processing unit 109 includes a keyboard or a mouse (not shown) for external input. The memory-control-signal processing unit 109 controls start and finish of fundus imaging. The memory-control-signal processing unit 109 includes a monitor (not shown), and can display a fundus image or specific information (left or right eye, personal data of a subject) specifying the eye to be inspected. The template image extracted by the memory-control-signal processing unit 109 is stored in the memory-control-signal processing unit 109 together with input specific information.

(Acquiring of Fundus Image 1)

FIG. 2 shows a flow for deciding a movement detecting template image for executing tracking using the fundus imaging apparatus of this embodiment. FIGS. 3A to 3C show extraction of a template image from a picked-up fundus image and pattern matching.

If an operator of this apparatus issues a command to start picking up a fundus image through the memory-control-signal processing unit 109, the light source 101 emits an illumination light 111. The memory-control-signal processing unit 109 starts scanning by the XY scanner 104 simultaneously with the command to start picking up a fundus image. The illumination light 111 is scanned by the XY scanner 104, passes through the lenses 106-1 and 106-2 and then enters the eye to be inspected 108 to execute raster scanning of the fundus 107 perpendicularly to an optical axis. The return light 112 reflected or scattered by the fundus 107 travels through the optical path in a reverse direction, passes through the half mirror 103 and enters the sensor 102. A signal converted into a voltage by the sensor 102 is transmitted to the memory-control-signal processing unit 109 to generate a first fundus image 301 (Step 202). In this embodiment, a fundus image of 2000 pixels×2000 pixels in size is acquired.

(Extraction of Template Image 1)

The memory-control-signal processing unit 109 extracts a template image for image evaluation from the generated first fundus image (Step 203). For the extraction of the template image, a characteristic point such as branching/crossing of blood vessels in a fundus image may be extracted, and not limited to this. Optic disk or the like may be used as a characteristic point. The extracted template image is stored in the memory-control-signal processing unit 109. A coordinate that specifies a position of the extracted template image on the first fundus image is simultaneously stored.

At least one template image may be extracted, but a plurality of template images are desirably extracted for more accurate image evaluation. Further, extracting areas of template images are desirably relatively separated from each other. In this embodiment, the first fundus image is divided into four areas around the center as an origin, and one template image is extracted from each area. Four template images 302, 303, 304 and 305 are acquired from the first fundus image.

Further, the size of the template image is not limited, but may be larger than a crossing/branching region of blood vessels. In this embodiment, the template image is 140 pixels×140 pixels in size. For extraction of a characteristic point, a generally implemented technique may be used, and detailed descriptions thereof will be omitted.

(Acquiring of Fundus Image 2)

When extraction of the template image is completed, the memory-control-signal processing unit 109 transmits a signal to start picking up a fundus image to the light source 101, the sensor 102, and the XY scanner 104 to pick up a second fundus image 311 (Step 204).

(Pattern Matching 1)

When the second fundus image 311 is acquired, points matching the template images 302, 303, 304 and 305 in the fundus image are searched (hereinafter referred to as matching) (Step 205). The searching point may be the entire second fundus image 311, but is desirably limited for image evaluation at higher speed. In this case, a point limited around the coordinate of the template image stored in the memory-control-signal processing unit 109 when the template image is acquired may be set as a searching point. In this embodiment, points of 280 pixels×280 pixels around the coordinates at which the template images are extracted are set as searching points 316, 317, 318 and 319, and compared and matched with the template images. At this time, matching is executed between a template image and a searching point in the same area as the template image. FIG. 10 shows a relationship between the template image and the searching point in this embodiment using reference numerals in FIGS. 3A to 3C. For a matching method, a generally implemented pattern matching technique can be used, and detailed descriptions thereof will be omitted.

The memory-control-signal processing unit 109 executes matching, determines how much the searching point is similar to the template image, and displays the result as similarity. To calculate similarity, for example, a correlation function can be used. Whether matching is completed is determined by separating the similarity at a certain threshold. A threshold may be arbitrarily set by an operator. Thus, determination is executed for four template images such that when the similarity is less than the threshold, it is determined that matching is not completed, and when the similarity is the threshold or more, it is determined that matching is completed. Further, it is determined whether matching is completed for all of the four template images (Step 206). At this time, similarly to Step 211 thereafter, the memory-control-signal processing unit 109 functions as a determination unit that determines whether the acquired fundus image is affected by movement of the eye to be inspected. Alternatively, the memory-control-signal processing unit 109 functions as a selecting unit that selects, among a plurality of acquired images, an image that is less affected by movement of the eye to be inspected, or an image that is affected at a threshold or less at which predetermined similarity is acquired.

If it is determined that matching is completed, it is determined that the first fundus image 301 and the second fundus image 311 are less affected by eye motion, and are the same fundus image, and a tracking template image is decided (Step 207). A characteristic point may be again extracted as a movement detecting template image for tracking, but a template image that has been extracted may be used. The eye motion (movement of the eye to be inspected) will be briefly described. The eye motion occurs from involuntary eye movement including tremor, flick, and drift, or movement of head. The result of the eye motion appears as one of discontinuity, expansion and contraction, and rotation of a fundus image, as an influence of movement of the eye to be inspected on the fundus image. In this embodiment, being less (or not) affected by eye motion (movement of the eye to be inspected) refers to that determination cannot be executed on the picked-up fundus image, that is, movement greater than resolution of the fundus image has not occurred during picking up of the fundus image. However, this is apparently not limited as described below.

In this embodiment, when all the template images match, it is determined that the template images are less affected by eye motion during image acquiring, and are the same fundus image, but not limited to this. A determination criterion may be arbitrarily set by the operator depending on conditions of the eye to be inspected or the patient.

In this embodiment, when the template images 302 and 303 do not match the searching points 316 and 317 on the second fundus image 311 (FIG. 3B), it is determined that either the first fundus image 301 or the second fundus image 311 is affected by eye motion during image acquiring.

(Acquiring of Fundus Image 3)

When it is determined that either the first fundus image 301 or the second fundus image 311 is affected by eye motion, the memory-control-signal processing unit 109 again acquires a fundus image as a third fundus image 321 (Step 209).

(Pattern Matching 2)

When acquiring of the third fundus image 321 is completed, matching is executed with the template images 302, 303, 304 and 305 (Step 210).

When it is determined that matching is completed, it is determined that the first fundus image 301 and the third fundus image 321 are less affected by eye motion, and are the same fundus image, and the second fundus image 311 is affected by eye motion. On the other hand, when matching is not completed herein, it is determined that the first fundus image 301 is affected by eye motion. When it is determined that matching is completed, a movement detecting template image for tracking is decided (Step 212). Also, a characteristic point may be again extracted as a movement detecting template image for tracking, but a template image that has been extracted may be used.

In this embodiment, the template images 302 and 303 do not match searching points 326 and 327 on the third fundus image 321 (FIG. 3C). This result shows that the first fundus image 301 from which the template images are extracted is affected by eye motion. Thus, the memory-control-signal processing unit 109 determines that the first fundus image 301 is not suitable for extraction of a movement detecting template image for tracking.

(Extraction of Template Image 2)

Since it is determined that the first fundus image 301 is not suitable for extracting a movement detecting template image for tracking, a movement detecting template image for tracking is extracted from the second fundus image 311 (Step 214). At this time, a third fundus image may be used for extracting a movement detecting template image for tracking. At this time, the memory-control-signal processing unit 109 functions as an extracting unit that extracts at least one characteristic point as a template image used for correcting the influence of movement of the eye to be inspected from a fundus image determined to be not affected by the movement of the eye to be inspected. The template image extracted by the memory-control-signal processing unit 109 in Step 214 is decided as a tracking template image (Step 215). The same process may be repeated to extract an optimum template image. For example, the memory-control-signal processing unit 109 determines whether the template image extracted from the second fundus image 311 matches images in searching points 326 to 329 on the third fundus image 321. When the images match, a movement detecting template image for tracking is decided from the second fundus image 311. On the other hand, when the images do not match, as in Step 209, a new fourth image is acquired and matching is executed between the second image and the fourth image as in Step 210. When matching is not completed, as in Step 214, a template image is extracted from the third image. As such, a new image may be acquired to decide a template image until matching is completed.

In this embodiment, the template image is extracted from the first image (Step 203), then the second image is acquired (Step 204), and a third image is acquired depending on the result of determination of matching (Step 206) (Step 209), but the second and third images may be previously acquired in Step 202 to execute the process. The fourth image may be also previously acquired.

The fundus image is evaluated as described above, and thus a fundus image that is not affected by eye motion can be selected to extract a movement detecting template image for tracking. Specifically, the memory-control-signal processing unit 109 determines that the fundus image is not affected by the movement of the eye to be inspected to extract and select a movement detecting template image for tracking. The memory-control-signal processing unit 109 functions as a detecting unit that detects movement of the eye to be inspected using the selected image. The memory-control-signal processing unit 109 functions as a correcting unit that corrects the influence of the movement of the eye to be inspected with reference to the template image to execute tracking. In this case, a reference coordinate may be set on the basis of the fundus image from which the template image is extracted or of a newly picked-up fundus image. This can reduce burdens on the operator and the patient during fundus imaging to execute tracking with high accuracy.

In this embodiment, the SLO has been described, but the same advantage can be obtained if this method is applied to a fundus image acquiring apparatus, in particular, an optical coherence tomography (OCT) or the like. This method may be applied to a fundus camera including a two-dimensional CCD as an imaging unit. In the above embodiment, the fundus image is described, but not limited to this. The embodiment may be applied to an anterior eye image. Embodiments described below may be also applied to an anterior eye image.

According to this embodiment, an ophthalmologic apparatus that reduces errors in extraction of a template image to increase matching accuracy in fundus imaging, reduce burdens on the operator and the patient, and can select a fundus image that is less affected by eye motion, and a control method thereof may be provided.

(Embodiment 2)

In this embodiment, a scanning laser ophthalmoscope (SLO) to which the present invention is applied will be described. In particular, an apparatus will be herein described that extracts template images from a plurality of picked-up fundus images, executes matching between the template images to evaluate the fundus images, and decides a movement detecting template image for tracking. With reference to FIGS. 1, 4 and 5, a method for evaluating fundus images using three fundus images will be particularly described in this embodiment.

This embodiment has the same configuration as Embodiment 1, and thus descriptions on the configuration will be omitted.

(Acquiring of Fundus Image)

When an operator issues a command to acquire a fundus image through the memory-control-signal processing unit 109, the ophthalmologic imaging apparatus 100 acquires a plurality of fundus images (Step 402). In this embodiment, three fundus images: a first fundus image 501, a second fundus image 511, and a third fundus image 521 are acquired. The operator may arbitrarily set the number of picked-up fundus images to two or more.

(Extraction of Template Image)

When imaging is completed, template images 502, 503, 504, 505, 512, 513, 514, 515, 522, 523, 524 and 525 are extracted from the fundus images (Step 403).

(Pattern Matching)

When extraction of the template images is completed, the memory-control-signal processing unit 109 executes matching using the template images extracted from the same area of the fundus images (Step 404).

In the first area of this embodiment, matching between the template images 502 and 512, between 502 and 522, and between 512 and 522 is performed. Matching is also executed in the second, third, and fourth areas.

Matching is executed by the memory-control-signal processing unit 109 to determine how much the template images extracted from the same area are similar, and the result is displayed as similarity. Whether matching is completed is determined by separating the similarity at a certain threshold. A threshold may be arbitrarily set by the operator. Thus, when the similarity is less than the threshold, it is determined that matching is not completed, and when the similarity is the threshold or more, it is determined that matching is completed. Whether the fundus image is affected by eye motion is determined by how much the templates match in each area (Step 405). In this embodiment, it is determined that images with templates in all areas matching are substantially the same image. However, not limited to the setting in this embodiment, a determination criterion of images may be arbitrarily set by the operator depending on conditions of the eye to be inspected and the patient. In this embodiment, as shown in FIGS. 6A to 6D, the template 523 on the third fundus image 521 does not match the template 503 on the first fundus image 501 and the template 513 on the second fundus image 511, and the other templates match. Thus, it is determined that the first fundus image 501 and the second fundus image 511 are substantially the same fundus image that is not affected by eye motion. On the other hand, it is determined that the third fundus image 521 is a fundus image affected by eye motion.

When it is determined that any images do not match, the process may return to (acquiring of fundus image) (Step 402), and a plurality of images may be again acquired.

(Decision of Template Image)

When matching is completed and it is determined that the image is not affected by eye motion, a characteristic point is extracted from the fundus image as a movement detecting template image for tracking. At this time, when a template image extracted for evaluation of the fundus image can be used for movement detection for tracking, there is no need to extract a new template image, and a template image that has been extracted may be used as a movement detecting template image for tracking.

The fundus image is evaluated as described above, and thus the fundus image that is not affected by eye motion can be selected to extract a movement detecting template image for tracking. This can reduce burdens on the operator and the patient during fundus imaging, thereby executing tracking with high accuracy.

In this embodiment, the SLO has been described, but the same advantage can be obtained if this method is applied to a fundus image acquiring apparatus, in particular, an OCT apparatus or the like. This method may be applied to a fundus camera including a two-dimensional CCD as an imaging unit.

(Embodiment 3)

In Embodiment 3, an apparatus will be described that acquires areas around a coordinate arbitrarily decided by an operator as template images from a first fundus image, rather than extracts a characteristic point as a template image, and executes matching on a plurality of fundus images for evaluation. In this embodiment, with reference to FIGS. 1, 7, 8 and 9, an apparatus will be particularly described that executes pattern matching on second and third fundus images using a template image selected from a first fundus image.

This embodiment has the same configuration as Embodiment 1, and thus descriptions on the configuration will be omitted. Descriptions on parts overlapping Embodiments 1 and 2 will be omitted.

(Acquiring of Fundus Image 1)

A first fundus image 801 from which a template image is acquired is acquired (Step 702). In this embodiment, a fundus image of 2000 pixels×2000 pixels in size is acquired.

(Extraction of Template Image 1)

When the first fundus image 801 is acquired, the memory-control-signal processing unit 109 extracts a template image for image evaluation (Step 703). An extracting area of the template image may be arbitrarily selected from a first fundus image, but an area expected to include much branching or crossing of blood vessels is desirably previously set as a characteristic point in the fundus image. At least one template image may be extracted, but a plurality of template images are desirably extracted for more accurate image evaluation. Further, extracting areas of template images are desirably relatively separated from each other. In this embodiment, the first fundus image is divided into four areas around the center as an origin, and one template image is extracted from each area. Four template images 802, 803, 804 and 805 (FIG. 8A) are acquired from the first fundus image. The template images are acquired around the center of the fundus image as the origin from the coordinates shown in FIG. 9. In this embodiment, the template image is 140 pixels×140 pixels in size.

(Acquiring of Fundus Image 2)

When the template image is extracted, the memory-control-signal processing unit 109 again acquires a fundus image for pattern matching (Step 704). At this time, at least one image may be acquired, but a plurality of images may be acquired to increase accuracy of image evaluation. The number of acquired fundus images is not limited, but may be arbitrarily decided by the operator. In this embodiment, a second fundus image 811 and a third fundus image 821 are newly acquired. In this embodiment, the fundus image is acquired after extraction of the template image, but a plurality of fundus images may be acquired in acquiring of the first fundus image (Step 702) and a part of the fundus images may be used.

(Pattern Matching)

When a plurality of fundus images are acquired, the memory-control-signal processing unit 109 executes pattern matching using the template image 802, 803, 804 and 805 extracted from the first fundus image 801 (Step 705) (FIG. 8B). Pattern matching is executed on the plurality of fundus images acquired in Step 704, and in this embodiment, executed on the second fundus image 811 and the third fundus image 821. Searching points in matching may be the whole of the second fundus image 811 and the third fundus image 821, but are desirably limited for image evaluation at higher speed. In this case, points limited around the coordinate of the template image stored in the memory-control-signal processing unit 109 in acquiring of the template image may be set as searching points. In this embodiment, points of 280 pixels× 280 pixels around the coordinate at which each template image shown in FIG. 9 is extracted are set as searching points 816, 817, 818, 819, 826, 827, 828 and 829 for matching. The memory-control-signal processing unit 109 determines whether matching is completed (Step 706).

The memory-control-signal processing unit 109 executes matching, determines how much the template images extracted from the same area are similar, and displays the result as similarity. Whether the fundus image is affected by eye motion is determined by how much the templates match in each area. In this embodiment, it is determined that images with templates in all areas matching are substantially the same image. However, not limited to the setting of this embodiment, a determination criterion may be arbitrarily set by the operator depending on conditions of the eye to be inspected or the patient. The result of matching is shown in FIGS. 11A to 11D.

In this embodiment, from the result of matching shown in FIGS. 11A to 11D, it is determined that the first fundus image 801 and the third fundus image 821 are substantially the same image. In this embodiment, it is determined that the first fundus image 801 and the third fundus image 821 are substantially the same image, but if all the images do not match, the process may return to Step 702 to restart the steps.

(Extraction of Template Image 2)

When matching is completed, and it is determined that the image is not affected by eye motion, a characteristic point is extracted as a tracking template image from the fundus image. In this embodiment, a characteristic point is extracted from the first fundus image 801. In this embodiment, the characteristic point is extracted from the first fundus image 801, but may be extracted from the third fundus image 821. Further, when matching is completed on a plurality of fundus images, a characteristic point may be extracted from an arbitrary fundus image selected from the matched fundus images.

The fundus image is evaluated as described above, and thus a fundus image that is not affected by eye motion can be selected to extract a movement detecting template image for tracking. This can reduce burdens on the operator and the patient during fundus imaging to execute tracking with high accuracy.

In this embodiment, the SLO has been described, but the same advantage can be obtained if this method is applied to a fundus image acquiring apparatus, in particular, an OCT apparatus or the like. This method may be applied to a fundus camera including a two-dimensional CCD as an imaging unit.

(Embodiment 4)

Figure 13:
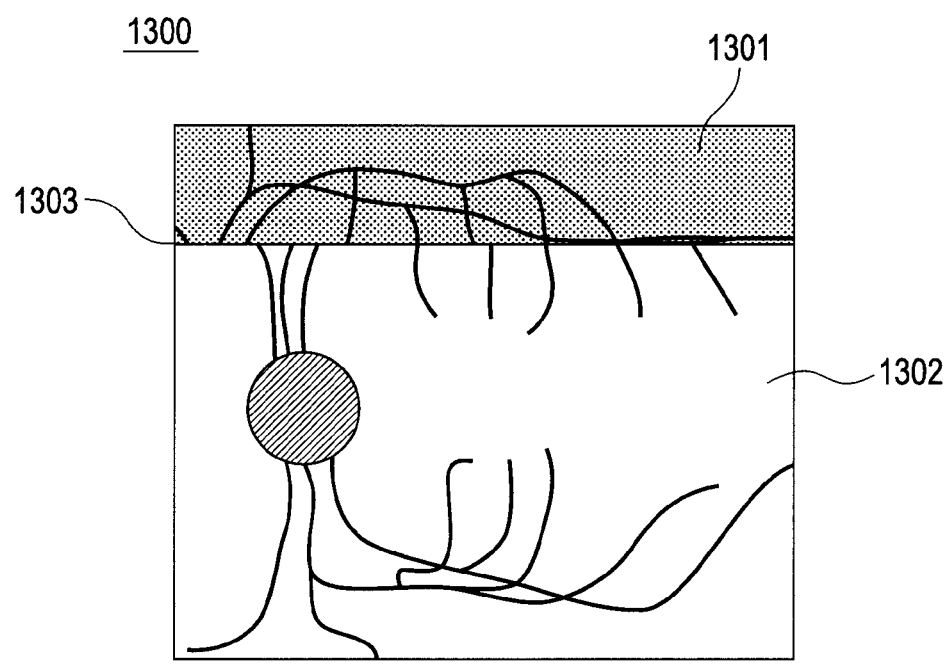
FIG. 13 illustrates evaluation of a fundus image in Embodiment 4 of the present invention.

In this embodiment, an apparatus will be described that acquires one fundus image, determines whether the fundus image is affected by eye motion, and decides a movement detecting template image for tracking. In this embodiment, with reference to FIGS. 1, 12 and 13, an apparatus will be particularly described that detects discontinuity in a fundus image to determine presence/absence of eye motion, and decides a movement detecting template image for tracking.

(Acquiring of Fundus Image)

One fundus image 1300 used for evaluation is acquired (Step 1202).

(Determination of Continuity)

A memory-control-signal processing unit 109 determines continuity of an image from the acquired fundus image 1300. The continuity of an image is determined by detecting whether characteristic areas in images for determination of continuity are continuous (Step 1203). In this embodiment, relatively large eye motion occurs during picking up of the fundus image 1300, and a fundus image portion 1302 is shifted from a fundus image portion 1301 with a discontinuous portion 1303 therebetween. When an eye is to be inspected, a blood vessel, yellow spot, and optic disk are considered to be characteristic areas, but not limited to them. In this embodiment, a blood vessel is set as a characteristic area to determine continuity. The method using the normalizing cross-correlation is used as an example for the method of determining the continuity using the characteristic area. In such method, the brightness value for respective pixel among acquired fundus image 1300 is calculated at the first and a profile of brightness value for one line is acquired. Thus acquired brightness value profile is compared with a profile of neighboring line, and the similarity thereof is calculated. The similarity is presented as a value within 0 to 1, and the value of 1 means a perfectly matching state. Although in the present embodiment, the threshold value of the similarity is set 0.6, such value can be arbitrarily set by an operator. A case wherein the similarity between the lines neighboring therewith is low means that the continuity therebetween is not ensured, and it is recognized that discontinuous portion caused by such as an eyeball movement exists in the fundus image. The method using the normalizing cross-correlation is specified above, but the present invention is not limited to this. Any of methods for determining the continuity can be preferably used.

When the memory-control-signal processing unit 109 determines that there is a discontinuous portion in one fundus image as in the fundus image 1300 (Step 1204), the process returns to Step 1202 to start acquiring of a fundus image. The memory-control-signal processing unit 109 repeats this until no discontinuous portion is detected in the acquired fundus image.

(Extraction of Template Image)

When determining that there is no discontinuous portion in the acquired fundus image (Step 1204), the memory-control-signal processing unit 109 extracts a movement detecting template image for tracking. Extraction of a template image is the same as in Embodiment 1 (Extraction of template image 1), and thus descriptions thereof will be herein omitted.

The fundus image is evaluated as described above, and thus a fundus image that is not affected by eye motion can be selected to extract a movement detecting template image for tracking. This can reduce burdens on the operator and the patient during fundus imaging to execute tracking with high accuracy.

In this embodiment, the SLO has been described, but the same advantage can be obtained if this method is applied to a fundus image acquiring apparatus, in particular, an OCT apparatus or the like. In this embodiment, a template image is extracted when it is determined that there is no discontinuous portion in the fundus image, but not limited to this. For example, when a discontinuous portion included in the fundus image is less than a predetermined value, the process may move to Step 1205, and when a discontinuous portion is a predetermined value or more, the process may move to Step 1202. Whether the discontinuous portion is a predetermined value or more is determined, for example, by determining whether the number of discontinuous portions in an image is a predetermined value or more.

(Other Embodiment)

The present invention is not limited to the above embodiments, but variants may be carried out without departing from the gist of the embodiments. For example, Embodiments 1 to 4 above may be arbitrarily combined. As an example of combination, Embodiments 1 and 4 may be combined. For example, when matching is not completed in Step 211, the process described in Embodiment 4 may be executed on the second image to decide a template image. When matching is not completed in Step 211, the process described in Embodiment 4 may be executed on the second image and the third image, and a template image may be decided from an image with fewer discontinuous portions. When the second image and the third image include discontinuous portions, for example, a plurality of new images may be acquired, and then the process described in Embodiment 1 may be executed on the plurality of images. Embodiments 1 to 4 are thus arbitrarily combined, thereby acquiring a more proper template image.

The present invention is also realized by executing the process below. Specifically, software (program) for realizing the function of the embodiments described above is supplied to a system or an apparatus via a network or various storage media, and a computer (or a CPU or an MPU) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-052296, filed Mar. 10, 2011, which is hereby incorporated by reference herein in its entirety.

What is claimed is:

1. An ophthalmologic apparatus comprising:
   an acquiring unit that acquires a plurality of images of an eye to be inspected;
   a determination unit that determines, using a processor, an image among the plurality of acquired images that is less affected by movement, during the image acquiring, of the eye to be inspected;
   a selection unit that selects an image which is a part of the image determined by the determination unit; and
   a detecting unit that detects movement of the eye to be inspected using the selected image.

2. The ophthalmologic apparatus according to claim 1, wherein the determination unit compares the plurality of images to determine the image that is less affected by movement of the eye to be inspected.

3. The ophthalmologic apparatus according to claim 1, wherein the determination unit determines the image that is less affected by movement of the eye to be inspected on the basis of at least one of discontinuity, expansion and contraction, and rotation of the image.

4. The ophthalmologic apparatus according to claim 1, wherein the determination unit compares a part of an area in the acquired image to determine an image that is less affected by movement of the eye to be inspected.

5. The ophthalmologic apparatus according claim 1, wherein the determination unit determines the image that is less affected by movement of the eye to be inspected on the basis of an image of a crossing or branching region of blood vessels included in the image of the eye to be inspected.

6. The ophthalmologic apparatus according to claim 1, further comprising an extracting unit that extracts at least one characteristic point from the image selected by the selection unit as the part of the image determined by the determination unit.

7. The ophthalmologic apparatus according to claim 6, wherein the characteristic point is an image of a crossing or branching region of blood vessels included in the image of the eye to be inspected.

8. The ophthalmologic apparatus according to claim 1, wherein when the determination unit cannot determine an image that is less affected by movement of the eye to be inspected, the acquiring unit again acquires an image of the eye to be inspected.

9. An ophthalmologic apparatus comprising:
   an acquiring unit that acquires an image of an eye to be inspected;
   a determination unit that determines whether an influence of movement of the eye to be inspected in the acquired image is a predetermined value or more; and
   a detecting unit that detects movement of the eye to be inspected using a part of the acquired image in response to the determination unit determining that the influence of movement of the eye to be inspected in the acquired image is less than the predetermined value.

10. The ophthalmologic apparatus according to claim 1, wherein the acquiring unit is a scanning laser ophthalmoscope (SLO) or an optical coherence tomography (OCT) unit.

11. A control method of an ophthalmologic apparatus comprising:
   acquiring a plurality of images of an eye to be inspected;
   determining, using a processor, an image among the plurality of acquired images that is less affected by movement of the eye to be inspected;
   selecting an image which is part of the image that is determined to be less affected by movement of the eye to be inspected; and
   detecting movement of the eye to be inspected using the selected image.

12. A recording medium for recording a program which causes a computer to execute the respective steps of the control method of the ophthalmologic apparatus according to claim 11.

13. An ophthalmologic apparatus comprising:
   an acquiring unit that acquires a plurality of images of a fundus of an eye to be inspected;
   a determination unit that determines, using a processor, an image among the plurality of acquired images that is less affected by movement, during the image acquiring, of the eye to be inspected;
   a selection unit that selects, as a standard image, an image which is a part of the image determined by the determination unit; and
   a detecting unit that detects movement of the eye to be inspected using the standard image.

14. An ophthalmologic apparatus comprising:
   an acquiring unit that acquires an image of a fundus of an eye to be inspected;
   a determination unit that determines whether or not a movement, during the image acquiring, of the eye to be inspected is equal to or larger than a predetermined value; and
   a detecting unit that detects the movement of the eye to be inspected using a standard image which is a part of the fundus image of the eye to be inspected, in response to the determination unit determining that the movement of the eye to be inspected in the fundus image is less than the predetermined value.

15. A control method of an ophthalmologic apparatus comprising:
   acquiring a plurality of images of a fundus of an eye to be inspected;
   determining, using a processor, an image among the plurality of acquired images that is less affected by movement, during the image acquiring, of the eye to be inspected;
   selecting, as a standard image, a part of the image determined to be less affected by movement of the eye to be inspected; and
   detecting movement of the eye to be inspected using the standard image.

16. A control method of an ophthalmologic apparatus comprising:
   acquiring an image of a fundus of an eye to be inspected;
   determining whether or not a movement, during the image acquiring, of the eye to be inspected is equal to or larger than a predetermined value; and
   detecting the movement of the eye to be inspected using a standard image which is a part of the fundus image of the eye to be inspected, in response to determining that the movement of the eye to be inspected in the fundus image is less than the predetermined value.

* * * * *